United States Patent [19]

Ratner et al.

[11] Patent Number: 4,824,237
[45] Date of Patent: Apr. 25, 1989

[54] VISION AND HAND/EYE COORDINATION EXERCISING AND TESTING MACHINE

[75] Inventors: Harvey Ratner, Silver Spring; Ronald Ratner, Rockville, both of Md.; Glenn A. Seifert, Southampton, N.Y.; Stephen Selwyn, Brooklyn, N.Y.; Marvin Zaro, New York, N.Y.

[73] Assignee: National Capital Center for Sports Vision Inc., New York, N.Y.

[21] Appl. No.: 826,961

[22] Filed: Feb. 7, 1986

[51] Int. Cl.$^4$ .......................... A61B 3/00; A63B 71/02
[52] U.S. Cl. ..................................... 351/203; 351/224; 273/26 R
[58] Field of Search .............. 351/203, 224, 223, 226; 273/26 A, 26 R, 185, 26 E, 1 GC

[56] References Cited

U.S. PATENT DOCUMENTS

| | | | |
|---|---|---|---|
| 4,146,311 | 3/1979 | Murr | 351/226 |
| 4,346,968 | 8/1982 | Melin et al. | 351/224 |
| 4,461,477 | 7/1984 | Stewart | 273/26 R |

Primary Examiner—Rodney B. Bovernick
Assistant Examiner—P. M. Dzierzynski
Attorney, Agent, or Firm—Epstein & Edell

[57] ABSTRACT

A vision and hand/eye coordination testing machine includes a front panel sub-divided into a grid-like array. Each array position is either a lamp position or a dummy position, the two being visually indistinguishable. Panel lamps are illuminated in one of three alternative modes, namely: a pursuit mode wherein lamps are illuminated according to a prescribed continuous pattern and the subject must follow the pattern by moving his/her eyes; a saccadic hand/eye mode wherein the subject focuses on a centrally located alternating fixator lamp and actuates a switch at array lamp positions; and a second hand/eye mode, similar to the saccadic mode, but the fixator lamp remains off. Timely switch actuations are counted and actuate respective indicators in a remote monitoring unit. In both hand/eye modes the lamps are illuminated in a random or other sequence unrelated to lamp position. A separate linear array of lamps is used in a fourth or sports mode in which the lamps extend toward the subject from the housing and are momentarily illuminated in sequence to simulate a ball moving toward the subject. The last lamp in the sequence is encapsulated in a bumper and may be struck with a hand, foot or instrument to effect a switch closure that is monitored relative to the time of illumination of the last lamp. The repetition rate of lamp illumination in all modes is adjustable.

27 Claims, 6 Drawing Sheets

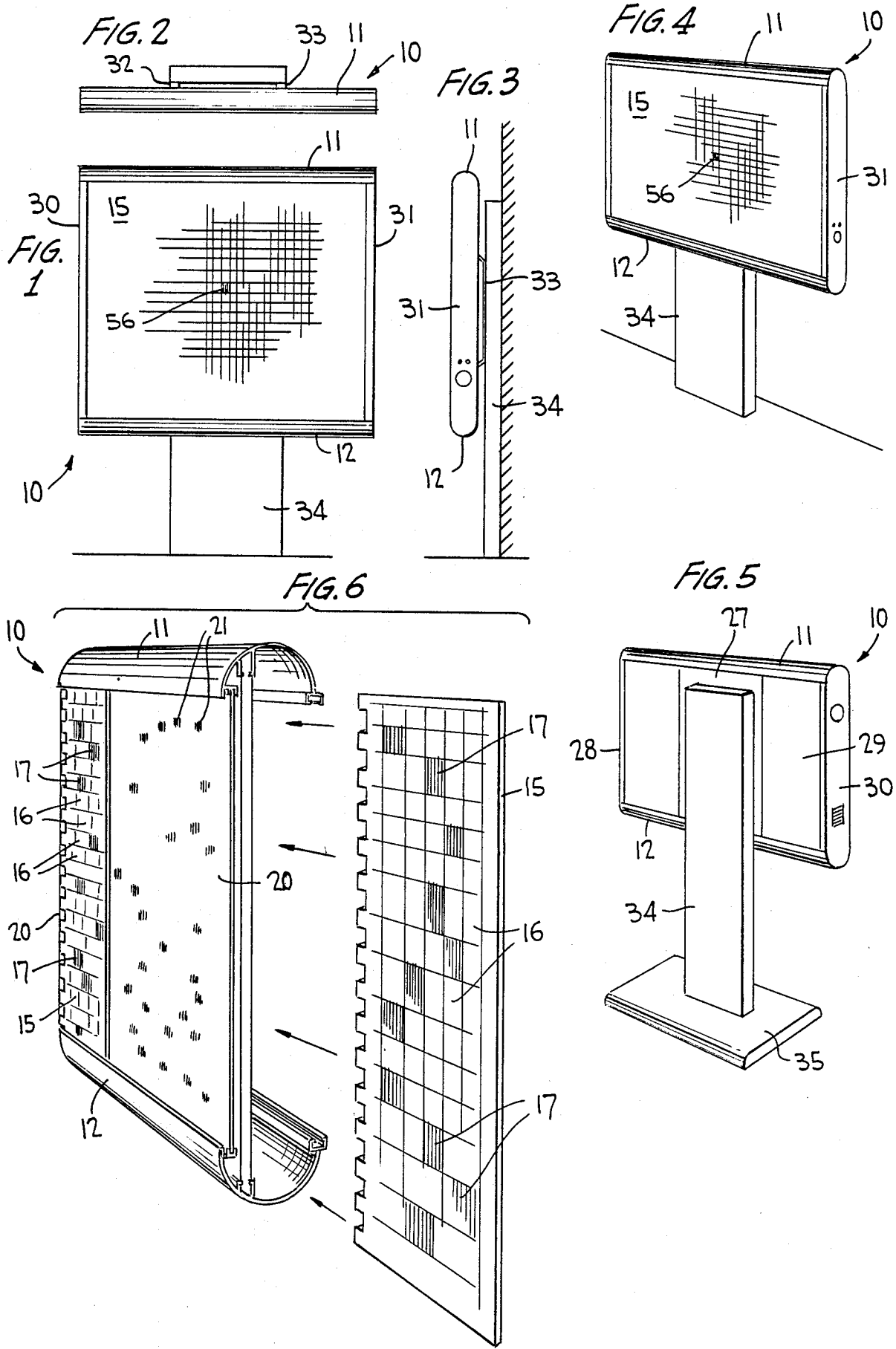

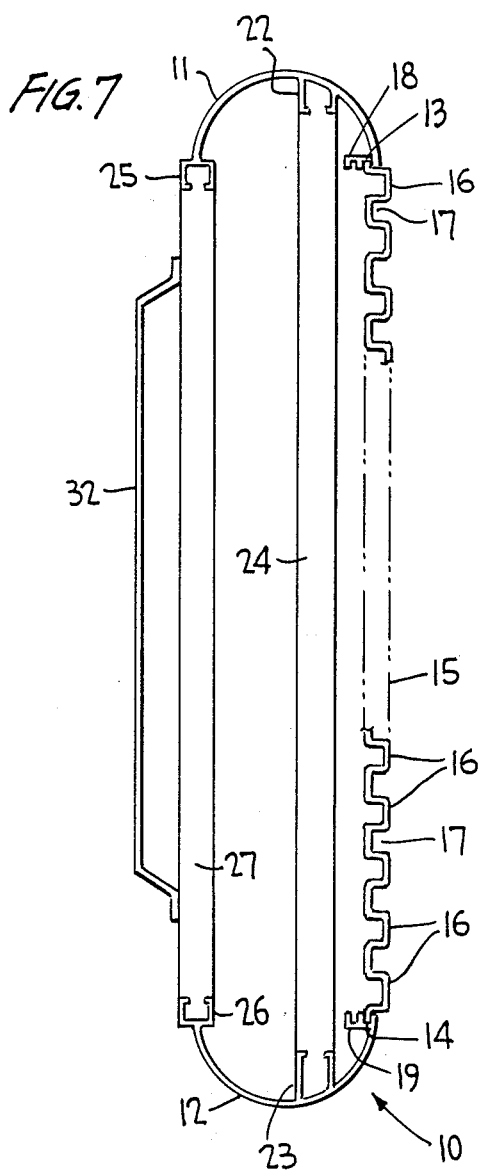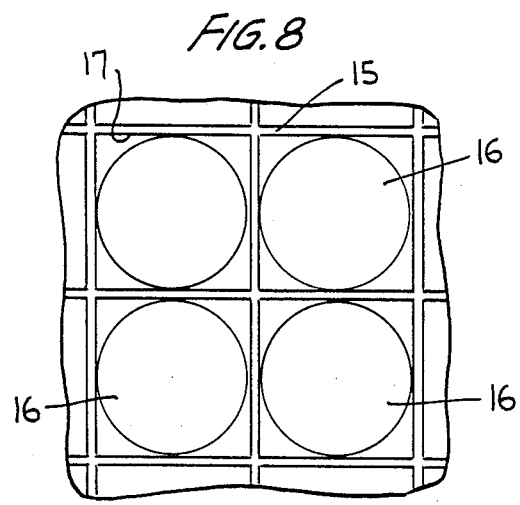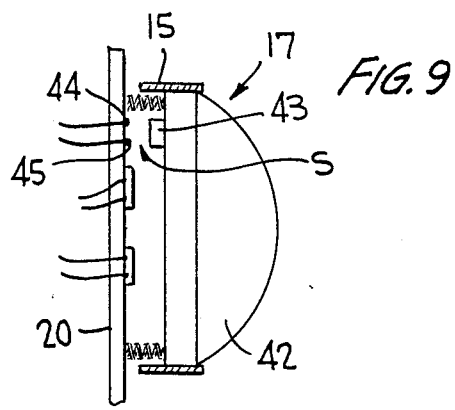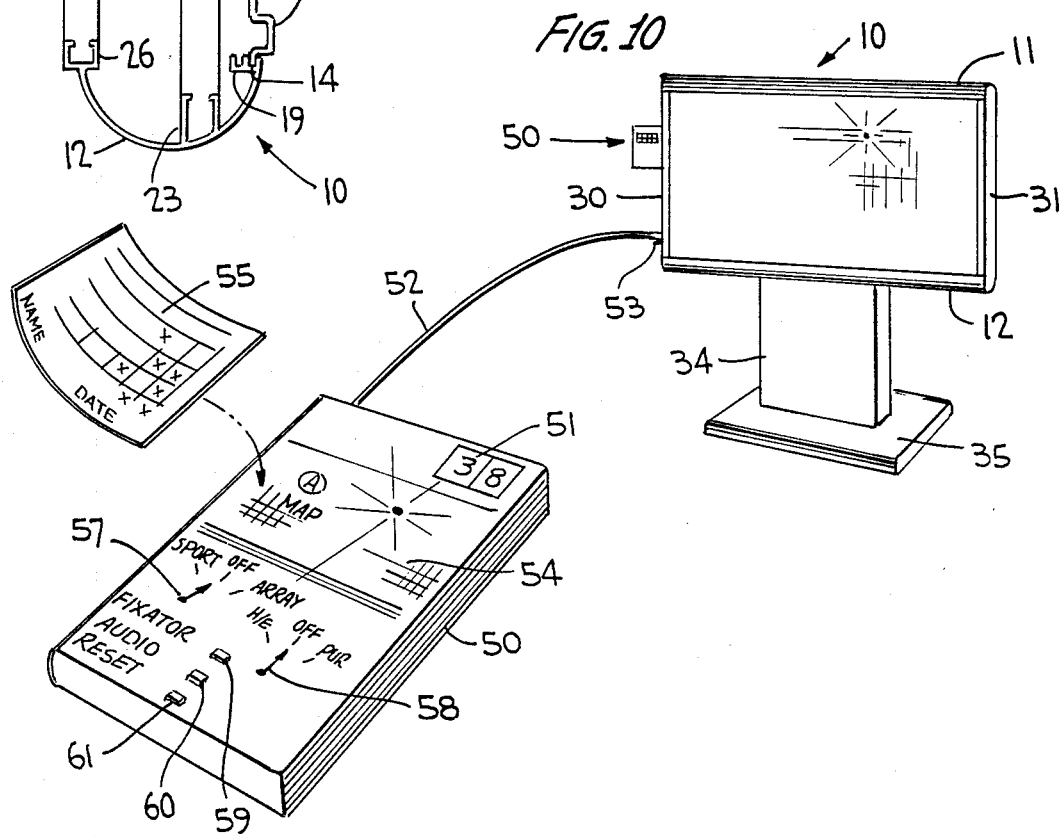

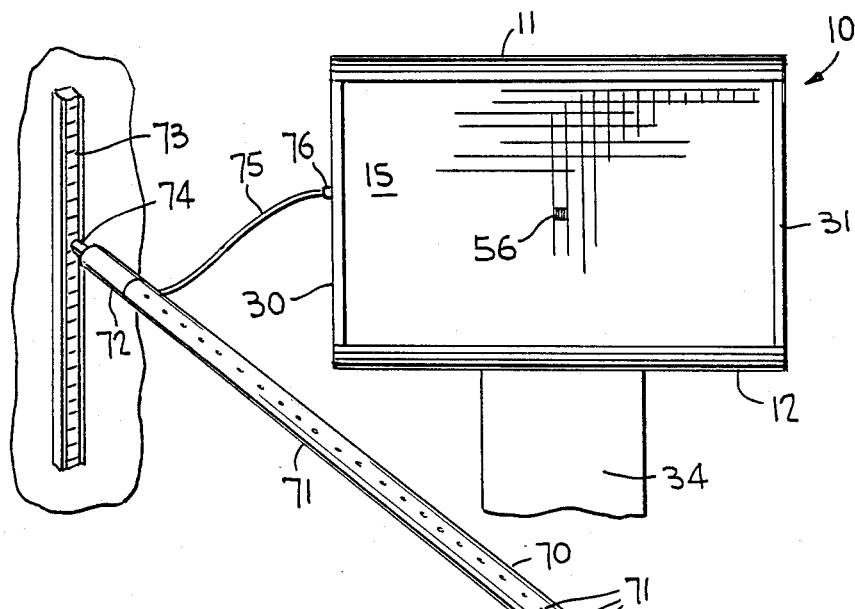
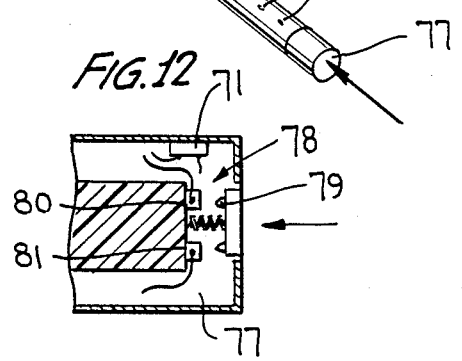
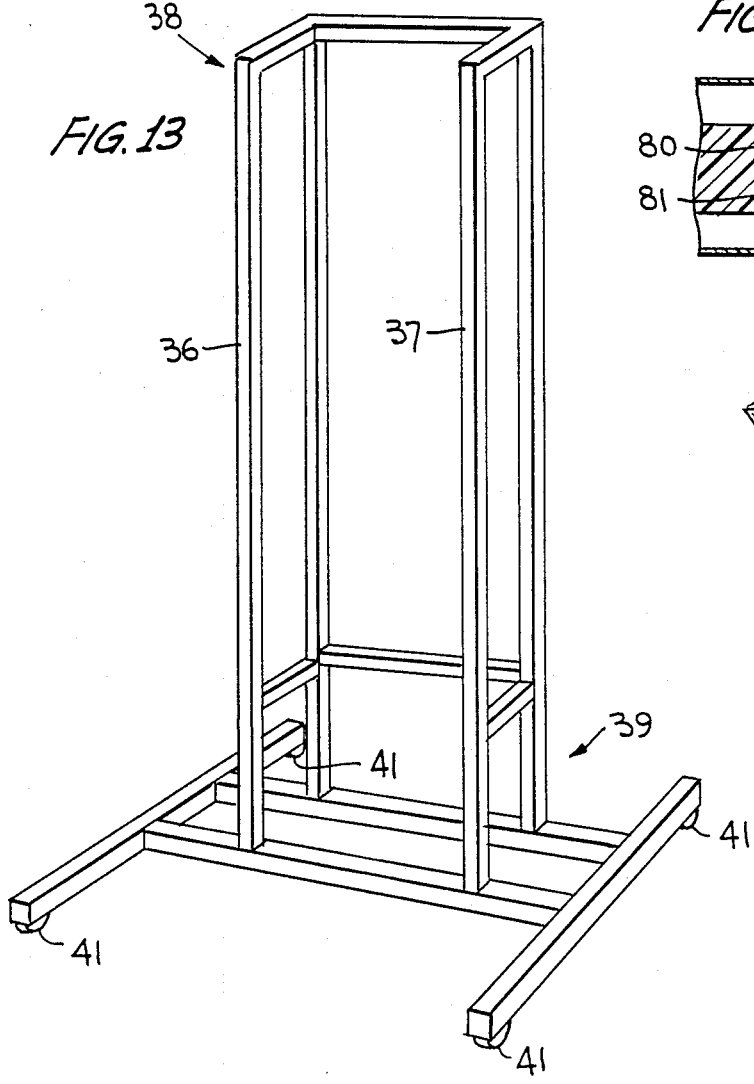
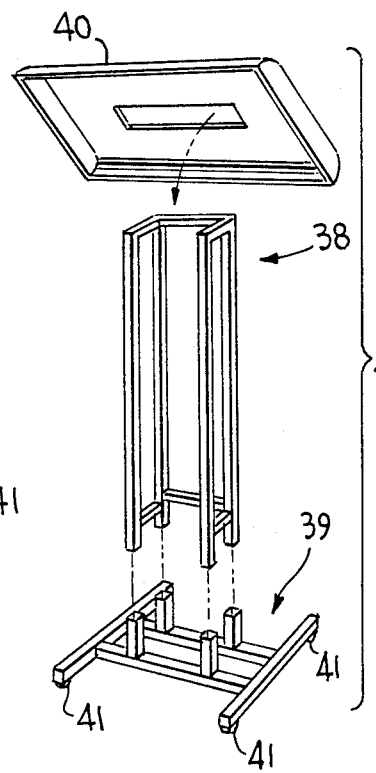

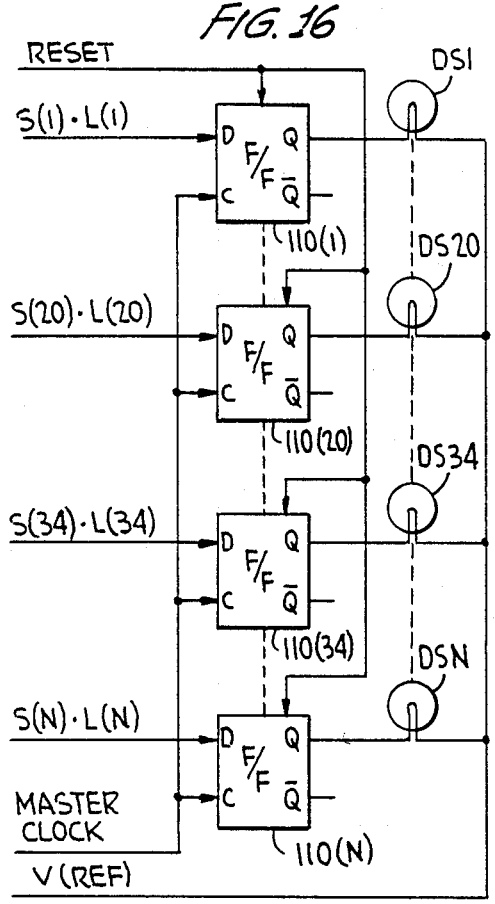
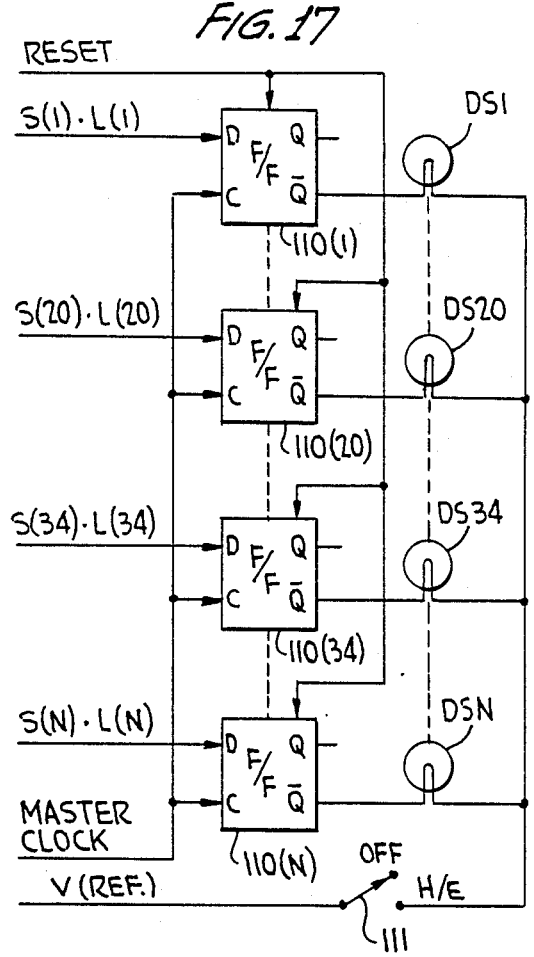
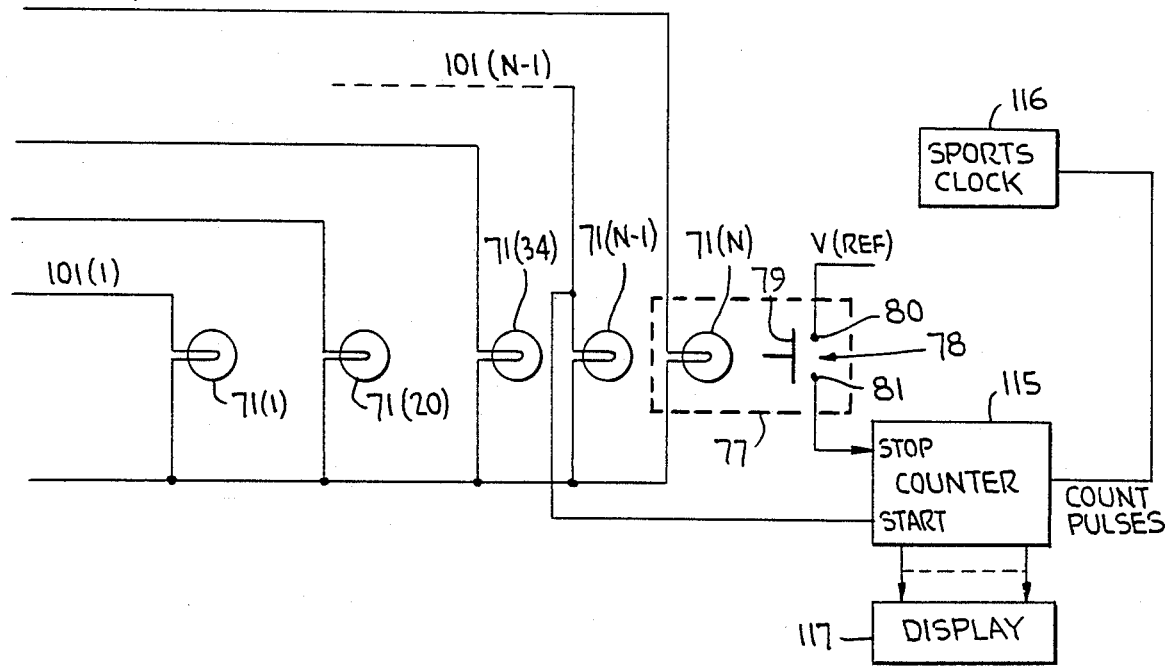

VISION AND HAND/EYE COORDINATION EXERCISING AND TESTING MACHINE

BACKGROUND OF THE INVENTION

1. Technical Field

The present invention relates to vision and hand-to-eye coordination testing and exercising. More particularly, the invention relates to a method and apparatus which can be utilized to test and exercise the strength and reaction time of optical muscles of a human subject. In addition, the invention relates to testing and exercising the hand-to-eye coordination and reaction times of a human subject.

2. Discussion of the Prior Art

A variety of different types of visual exercising devices exist in the prior art. For examples of such devices, reference is made to the following U.S. Pat. Nos. 2,224,776 (Bermann), 2,476,708 (Day), 2,718,227 (Powell), 3,258,303 (Silverstein), 3,545,847 (Pietrini), 4,294,522 (Jacobs) and 4,464,027 (Cooper). Of these, the device disclosed in the Powell patent is of particular interest. In that device, a plurality of spaced lamps on a panel are sequentially lighted in alternation with a central or fixator lamp. A human subject initially visually focuses on the fixator lamp and is required, as part of the exercise, to change his/her focus to each peripheral lamp and back to the fixator lamp as the lamps are momentarily illuminated. This procedure exercises the subject's ocular muscles.

A similar concept is employed in a machine sold under the name Eyespan 2064 by Monark America of Redmond, Wash. In that machine, however, the panel lamps are in the form of switches which the subject can push to extinguish the lamp and thereby exercise/test his/her hand-to-eye coordination in addition to his/her eye muscles.

Although the devices described above do serve their intended purposes to some extent, they suffer from a similar disadvantage which reduces their efficiency. Specifically, both prior art devices have the lamp locations spaced and clearly designated on the instrument panel. The subject, therefore, finds it relatively easy to focus upon and/or activate an illuminated lamp since there is nothing but panel surrounding that lamp. In addition, the subject can form a general idea as to where the illuminated lamp will be in advance of actual illumination of that lamp.

With respect to exercising/testing hand-to-eye coordination, it is difficult to keep track of a subject's success and progress with the prior art devices. An optometrist or trainer must stand near the device and quickly note any and all lamps which are not extinguished by the subject within a predetermined period of time. This becomes difficult, particularly if the illumination repetition rate is high.

Another device for exercising/testing hand-to-eye coordination, particularly for athletes, is disclosed in U.S. Pat. No. 4,461,477 (Stewart). In that device, designed primarily for testing the response time of a batter to a pitched baseball, lamps are momentarily and successively illuminated along a path which, in one embodiment extends toward a batter. A plurality of vertically directed light beams are positioned proximate "home plate" and are momentarily interrupted as the batter/subject swings his bat. The time difference between beam interruption and illumination of the last lamp in the string is monitored as a measure of the subject's response to the simulated pitch. A disadvantage associated with this device is the fact that the batter/subject merely interrupts a light beam with the swing of the bat; that is, no solid object is struck by the bat. The last lamp in the sequence is not disposed at the point of impact; this displacement from the point of impact results in a built-in error in the measurement of time between illumination of the last lamp and the "hitting" of the simulated pitch at the displaced impact location. Moreover, the batter's swing is not realistic since it encounters n resistance.

OBJECTS AND SUMMARY OF THE INVENTION

It is therefore an object of the present invention to provide a vision and hand-to-eye coordination exercising and testing device in which the positions of sequentially illuminated lamps on a panel are not readily evident. It is a further object of the invention to incorporate into that device an arrangement for simulating a thrown or kicked object and accurately measuring the time a subject strikes the object at an actual impact point.

A further object of the present invention is to provide a method and apparatus for exercising and testing optical muscles and hand-to-eye coordination in a variety of different modes.

It is yet another object of the present invention to permit accurate and reliable measurement of a subject's progress and success in exercising and testing hand-to-eye coordination with a device of the type in which lamps on a panel are individually and momentarily illuminated in sequence.

In accordance with the present invention a panel is sub-divided into a plurality of lamp positions and dummy positions oriented in a predetermined array. In the preferred embodiment the array is a grid of rows and columns in which the dummy positions outnumber the lamp positions by a ratio of at least ten-to-one and preferably on the order of nineteen-to-one. Importantly, the dummy positions and lamp positions are visually indistinguishable when viewed from in front of the panel so that a subject using the device cannot determine locations in the array to be illuminated. The lamp positions are sequentially and momentarily illuminated in an order determined by the selected operating mode. In one mode, designated the pursuit mode, the lamps are illuminated in a prescribed sequence, preferably corresponding to a continuous path or pattern, such as a spiral, in which successively illuminated lamps are located proximate one another. In this mode the subject is required to visually follow the pattern of sequentially illuminated lamps to exercise his/her ocular muscles. In a second mode, designated the hand/eye saccadic mode, the lamps are illuminated momentarily in a sequence which is preferably random (i.e., unrelated to lamp array positions) but may correspond to a positional sequence. The subject is required to actuate a switch at the illuminated lamp while the lamp is illuminated. If the switch is actuated while its associated lamp is illuminated (or within a predetermined time after onset of illumination), a count pulse is generated and applied to a counter to provide an accumulated count representing the subject's success during the illumination sequence. Timely switch actuation is also utilized to activate (or deactivate) indicators located at a remote unit (as used by an optometrist or trainer) and arranged in a map or pattern corresponding to the lamp positions in the panel array. Thus, as each switch is timely actuated, a count is registered and a corresponding map indicator is activated. After the illumination sequence the activated indicators clearly show which panel switches were timely actuated and which were not. A third mode, designated the hand/eye fixator mode, utilizes a fixator lamp located centrally of the panel and periodically illuminated at a lower repetition rate than the lamps in the array. The array lamps are momentarily illuminated in sequence (random or patterned) and the subject must actuate the switch for each illuminated array lamp while the fixator lamp is illuminated. For each illumination of the fixator lamp, plural array lamps may be illuminated and, depending upon the subject's hand-to-eye coordination, the switch corresponding to some or all of these may be actuated. The map indicators are capable of indicating which of the illuminated panel array switches were not timely actuated, or which panel switches were actuated in the absence of simultaneous illumination of both the fixator lamp and the array lamp associated with the actuated switch. In order to permanently record a subject's performance in either of the hand/eye modes, a pre-printed transparent sheet is placed over the map s that the map locations on the sheet may be marked by the trainer or optometrist to designate map indicators that were activated or not activated.

A further mode, designated the sports mode, does not make use of the panel lamps and switches. Instead, a multiplicity of lamps extend in a linear array along a pole which can be secured to extend horizontally at an adjustable height. The linear array may be plugged into the panel housing so that timing pulses used in the other operating modes may be employed to momentarily and sequentially illuminate the lamps in the linear array. These lamps are spaced and illuminated in a sequence to simulate a thrown, kicked or otherwise impelled ball or projectile. The lamp at the distal end of the pole is encapsulated in a clear, shock-absorbent and protective bumper and is associated with an impact switch that is momentarily closed when the bumper is impacted such as by a bat, tennis racquet, foot, etc. A subject thus strikes the last lamp directly, rather than striking a location spaced from the lamp, and encounters some resistance to the striking force. The bumper and a shock absorber disposed at the pole mounting permit this resistance to closely simulate that resistance which would be typically encountered by a bat hitting a pitched ball, a racquet hitting a moving tennis ball, a foot kicking a moving soccer ball, etc. The time of switch closure is monitored relative to the time of illumination of the last lamp, and indicators are activated to designate whether the impact was early, late or at the proper time.

BRIEF DESCRIPTION OF THE DRAWINGS

The above and still further objects, features and advantages of the present invention will become apparent upon consideration of the following detailed description of specific embodiments thereof, especially when taken in conjunction with the accompanying drawings wherein like reference characters in the various figures are utilized to designate like components, and wherein:

FIG. 1 is a front view in elevation of a housing and panel for one embodiment of the present invention;

FIG. 2 is a top view in plan of the apparatus of FIG. 1;

FIG. 3 is a side view in elevation of the apparatus of FIG. 1;

FIG. 4 is a view in perspective of the apparatus of FIG. 1, showing the apparatus mounted on a wall;

FIG. 5 is a rear view in perspective of the apparatus of FIG. 1, showing the apparatus mounted on a floor;

FIG. 6 is an exploded view in perspective of the panel portion of the apparatus of FIG. 1;

FIG. 7 is a side view in vertical section of the panel illustrated in FIG. 6;

FIG. 8 is a detailed front view in elevation of four array positions of the panel illustrated in FIG. 6;

FIG. 9 is a side view in partial section showing one of the array positions illustrated in FIG. 8;

FIG. 10 is a view in perspective showing the remote control and indicator unit utilized by an optometrist or trainer in conjunction with the apparatus of FIG. 1;

FIG. 11 is a view in perspective and partially diagrammatic of the apparatus of the present invention employed in the sports mode;

FIG. 12 is a side view of the distal end portion of the pole employed in FIG. 11 for the sports mode;

FIG. 13 is a view in perspective of an alternative mounting arrangement for the panel unit of FIG. 1 whereby to permit vertical adjustability of the panel;

FIG. 14 is an exploded view in perspective of the apparatus of FIG. 13;

FIG. 16 is a schematic diagram of an electrical circuit employed to activate individual indicators at the map unit of FIG. 10

FIG. 17 is a schematic diagram of an alternative embodiment of the circuit of FIG. 16;

FIG. 18 is a schematic diagram of the circuit employed in the sports mode of the device of the present invention;

DESCRIPTION OF THE PREFERRED EMBODIMENTS

Figure 15:
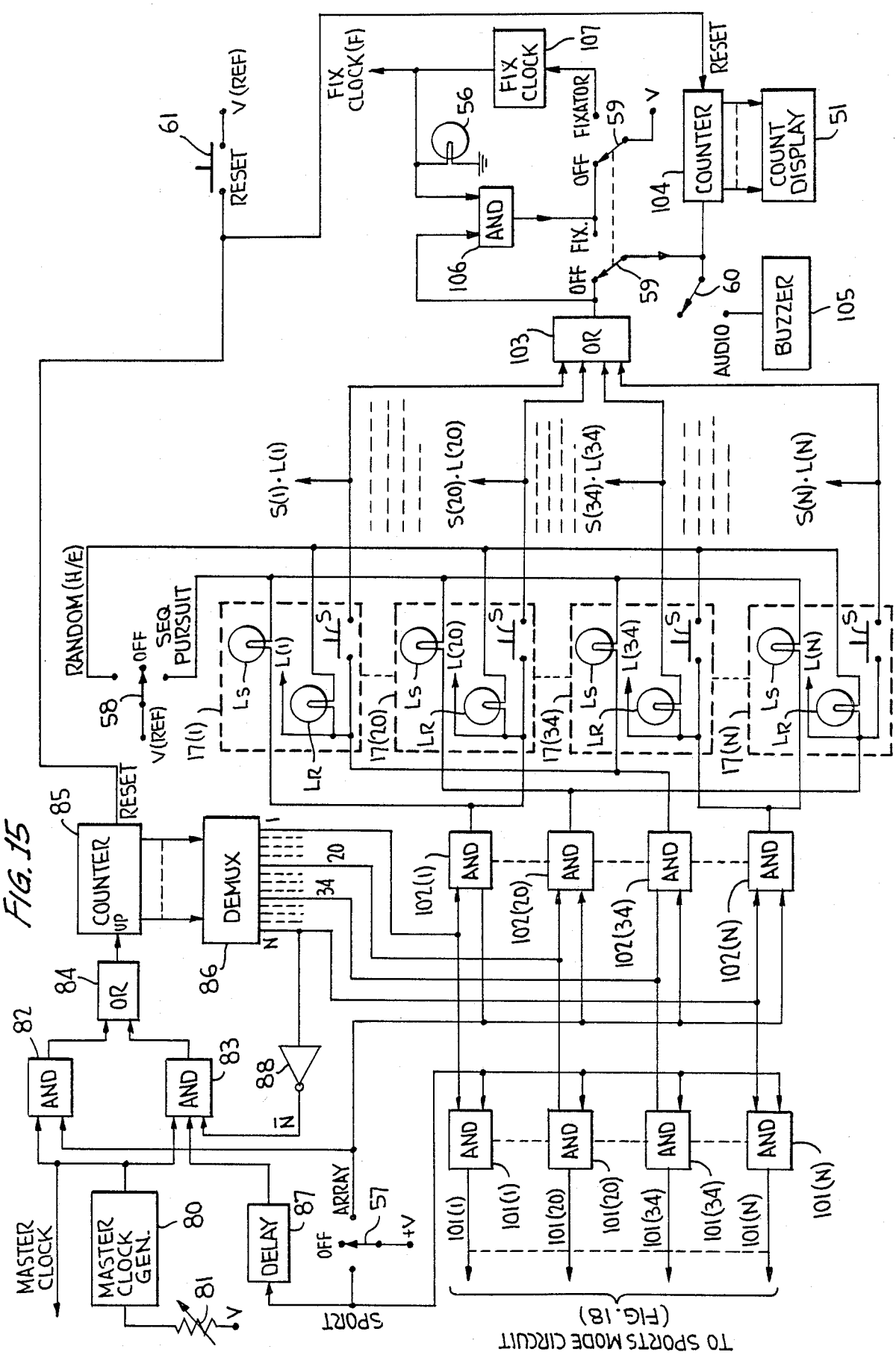
FIG. 15 is a schematic diagram of the basic timing and logic circuitry employed to illuminate the lamps at the panel in the apparatus of FIG. 1.

Referring specifically to FIGS. 1-7 of the accompanying drawings, a housing 10 includes a top member 11 and a similarly configured bottom member 12 having convex outer surfaces. Members 11 and 12 are preferably formed of extruded aluminum having a satin finish and include integrally formed tracks disposed within and extending transversely across the housing. Forward tracks 13 and 14, formed as part of top member 11 and bottom member 12, respectively, are vertically aligned to receive a screen 15, defining a grid pattern (i.e., vertical columns, horizontal rows) of lamp positions and dummy positions. Screen 15 constitutes part of the front panel of housing 10 and is preferably molded from polycarbonate material with openings at the lamp positions 17 and with integrally formed simulated switch covers- /actuators 16 covering the dummy positions. As an example of the size of the individual grid locations, in the preferred embodiment such locations are approximately one and one-quarter inches square. A second set of vertically aligned tracks 18, 19 slidably receive an electronic component board 20 disposed immediately behind screen 15 and constituting the other part of the housing front panel. Component board 20 includes multiple spaced lamp positions 21 aligned with lamp position openings 17 in screen 15. The lamp positions on the front panel are disposed in a predetermined array and are interspersed with dummy positions It is preferred that the individual lamp positions are separated from one another in each column and row by at least one dummy position. The dummy positions outnumber the lamp positions by at least ten-to-one and, in the preferred embodiment there are a total of twelve hundred total grid positions with only sixty of these being lamp positions. Importantly, as described below, the lamp positions and the dummy positions are visually indistinguishable when viewed from in front of the front panel of housing 10.

Additional aligned tracks 22, 23 engage a support structure 24 in the form of a wooden, plastic or metal board employed to provide structural support and rigidity for the housing 10. Support structure 24 is disposed behind and spaced from the component board 20. A set of aligned rear tracks 25, 26 receive a rear support panel 27 also made of opaque plastic, wood or metal and employed to impart rigidity and structural support to the housing. In addition, panel 27 serves as the rear panel for the housing and includes doors 28, 29 for providing access to the housing interior. The sides of the housing 10 are enclosed by respective sidewalls 30, 31 preferably made of opaque plastic material and including various electrical receptacles through which external parts of the system can be electrically interconnected to components inside the housing on component board 20.

Two metal brackets 32, 33 are secured to the outside surface of rear panel 27 to permit the housing to be supported with its front panel vertically oriented In the deployment illustrated in FIGS. 1–5, brackets 32, 33 engage a support structure 34 adapted to secure the housing 10 to and/or against a vertical wall. Alternatively, support structure 34 may itself be supported on a pedestal 35, as illustrated in FIG. 5, to deploy the housing 10 in a free-standing orientation.

Alternative mounting for housing 10 is provided by the frame structure 38 illustrated in FIGS. 13 and 14 wherein a pair of vertical and mutually parallel tracks 36, 37 are disposed to receive brackets 32, 33, respectively, in slidable engagement. With this mode of deployment the brackets 32, 33 can be clamped in space at any desired height along tracks 36, 37 to permit adjustment of the height of housing 10 and its front panel. The frame structure 38 mounts on a base 39 having a cover 40, the base being provided with casters 41 that are lockable and permit the frame to be easily moved about.

As illustrated in FIG. 8, the lamp positions 17 and dummy positions 16 of the grid are visually indistinguishable when viewed from in front of housing 10. The lamp positions, however, as best illustrated in FIG. 9, include a movable switch actuator 42 slidably disposed in the opening 17. Switch actuator 42 is identical in appearance, as viewed from in front of housing 10, to simulated switch covers/actuators 16 formed integrally with molded screen 15. The differences reside in the fact that: (1) movable switch actuator 42 is engaged for slidable movement within the screen in a direction perpendicular to the front panel, whereas simulated or dummy actuators 16 are immovable; and (2) active lamps and switch contacts are provided behind the actual switch actuators 42, whereas no active components need be provided behind the dummy positions. As illustrated in FIG. 9, each actuator 42 is mounted in a spring-bias relation to component board 20 so that the actuator is normally maintained in an extreme position remote from the board. If the actuator 42 is depressed towards the board 20 a metal contact 43, carried by actuator 42, bridges contacts 44, 45 on component board 20 to close switch S for that lamp position. That lamp position is also provided with two lamps (e.g., light-emitting diodes) $L_S$ and $L_R$. The switch actuators 42 and the simulated actuator 16 are made of smoked polycarbonate material which presents an opaque appearance if not back-lighted. However, the actuator 42 transmits and diffuses light from either of lamps $L_S$ and $L_R$ to render the emitted light visible from in front of housing 10. In the preferred embodiment lamps $L_R$ and $L_S$ emit red light.

As described in greater detail below in relation to the electrical schematic diagrams of FIGS. 15–22, depending upon the operating mode, the lamp positions at the front panel are momentarily illuminated in a prescribed sequence. In the pursuit mode, lamps $L_S$ are illuminated sequentially in a continuous moving pattern. In this mode the subject stands in front of the front panel with his/her head facing substantially centrally of the panel. The subject follows the moving pattern with his/her eyes in an exercise/test of ocular muscles. In the hand-/eye mode, the lamps $L_R$ are illuminated in a random sequence (e.g., a sequence in which successively illuminated lamps are not adjacent one another in the array). In this mode the subject is required to push the actuator 42 associated with an illuminated lamp $L_R$ during the illumination or within a prescribed period of time after the onset of such illumination. For each timely actuation of a switch S, a count pulse is generated and applied to a counter. An accumulated count of these pulses is registered at a count display 51 located at a remote map unit 50 (illustrated in FIG. 10) used by a trainer or optometrist working with the subject. A count display may also be provided at the front panel of housing 10. Map unit 50 includes a cable 52 terminating in a multipin plug 53 received in a receptacle at housing sidewall 30 to provide electrical signalling between the housing and the map unit 50. Alternatively, such signalling may be provided by radio transmission Map unit 50 may be stored at an appropriate mounting at sidewall 30 as illustrated in FIG. 10.

The map unit 50 is also provided with a map array 54 of indicators, such as lamps, positioned in accordance with the array of lamp positions at the front panel of housing 10. Each indicator in the map array 54 corresponds to a respective lamp $L_R$ at screen 15 and is activated or deactivated as an indication of successful (i.e., timely) actuation of each lamp switch S at the front panel of housing 10. After a sequence of illumination of lamps $L_R$, the map array 54 provides an indication of which switches S were timely actuated and which were not. In order to provide a permanent record of this result, a transparent sheet 55 is superposed on the map array 54. Sheet 55 is pre-printed with marks sub-dividing the sheet into areas corresponding to respective indicators in the map array 54. At the end of a random sequence in which all of the lamps $L_R$ have been illuminated, the areas of sheet 55 which overlie activated (or unactivated) map indicators can be marked with a pen or pencil to provide the desired permanent record.

In another operating mode of the system a blue fixator lamp 56 at the housing panel is turned on and off at a repetition rate which is slower than the repetition frequency of lamps $L_R$. The fixator lamp 56 is positioned on component board 20 substantially centrally of the front panel. The subject is required to focus (i.e., fixate) on the fixator lamp 56 and, using peripheral vision hit actuator 42 to actuate switch S for each lamp $L_R$ that is illuminated during the time that the fixator lamp 56 is illuminated. Timely actuation of the switch S results in a count pulse being counted so a to increment the count at display 51 of the map unit. Additionally, an indicator in the map array 54 is activated each time its corresponding lamp $L_R$ is illuminated while the fixator lamp 56 is illuminated and the corresponding switch S is not timely activated. The map array indicators 54 may also be activated each time a switch S is actuated when its corresponding lamp $L_R$ is not illuminated.

Map unit 50 is also provided with a plurality of switches 57, 58, 59, 60 and 61. Switch 57 is a three-position switch permitting selection of a sports mode (described below) or an array mode (i.e., the modes described above in which the lamps at the front panel are sequentially illuminated). The purpose of switch 58 is to permit selection between random (H/E, for hand-to-eye) and pursuit (sequential pattern) illumination sequences of the lamps at the front panel of housing 10. The fixator switch permits selection of the fixator mode in which the fixator lamp 56 is alternated on and off. The audio switch 60 enables a device such as a buzzer to provide an audible indication each time a timely actuation of a switch S is effected. Reset switch 61 permits various electronic components at the component board 20 to be reset.

The sports mode involves the apparatus illustrated in FIGS. 11 and 12 to which specific reference is now made. A pole or rod 70 has a multiplicity of lamps 71 mounted thereon in a linearly spaced array. The rod 70 is rigid and sufficiently strong to resist breakage when used in the manner described below. The proximal end of rod 70 is provided with a shock absorber 72 for absorbing impact applied axially to the rod. Shock absorber 72 is provided with a clamp 74 adapted to be affixed to a vertically-extending track 73 at a height consistent with the particular exercise/test for which the apparatus is being used. Track 73 may be mounted on a wall or on the frame structure 38 (FIGS. 13, 14) by any suitable attachment. A cable 75 extends from rod 70 and terminates in a plug which is inserted into a receptacle in sidewall 30 of housing 10. Timing signals for sequentially and momentarily illuminating lamps 71 are derived from circuitry on component board 20 in housing 10 and transmitted to the lamps 71 via cable 75.

The last lamp 71 at the distal end of rod 70 is encapsulated in a clear, preferably collapsible, silicone bumper 77 so that the lamp can be seen when it is illuminated. Bumper 77, illustrated in greater detail in FIG. 11, includes an impact switch 78 disposed therein having a movable bridge contact 79 and two stationary contacts 80, 81. Forceful impact applied axially t the rod 70 at its distal end (i.e., in the direction of the arrows in FIGS. 10 and 11) forces movable contact 79 into engagement with stationary contacts 80, 81 to provide a switch closure. Wires for the switch 78 and lamps 71 are passed within rod 70 via cable 75 to housing 10.

The sports mode permits a subject to strike a simulated pitched ball or other moving object. Lamps 71 are illuminated in a sequence from the proximal end at shock absorber 72 to the distal end at bumper 77. The subject swings a bat, tennis racquet, or the like, to impact bumper 70 with a normal swing, the object of the swing being to strike the bumper when the last lamp 71 is illuminated. Switch 78 closes at the time of impact and is monitored, in the circuit of FIG. 18, to provide an indication as to whether the subject's swing was early, late or properly timed relative to the illumination of the distal lamp 71. It will be appreciated that the sequence of illumination of lamps 71 can be used to simulate any sports activity, such as a thrown baseball, a stroked tennis ball, a moving hockey puck, a kicked soccer ball, etc., and the subject can strike the bumper 77 with a bat, tennis racquet, hockey stick, foot, hand, etc. The purpose, of course, is to test/exercise the timing and coordination of the subject In this mode, as in the modes described above, the repetition rate of lamp illumination is adjustable so that pitches of different speeds can be simulated.

Although the bumper 77 is illustrated as having a cross-sectional configuration corresponding to that of rod 70, it is clear that any configuration may be employed. In particular, the bumper may be configured as a ball or puck of appropriate size for the sport being tested. The bumper material, combined with the effects of shock absorber 72, provide a resistance at impact to the subject's swing, which resistance simulates the resistance provided by the thrown ball or other object being simulated.

Typical electrical circuitry for effecting the operational modes described above is illustrated in FIGS. 15-23. For purposes of the illustrated embodiment and the present description, a positive logic convention is employed wherein AND and OR gates and other elements are activated by positive voltage levels It is to be understood that this convention is by way of example only and that other logic conventions may be employed, as desired, to effect the specified modes of operation.

Referring specifically to FIG. 15, a master clock pulse generator 80 provides a train of clock pulses with a repetition rate determined by the resistance setting of resistor 81. The master clock pulse generator may, for example, be a standard integrated circuit model 555. For the present system the repetition rate of the master clock pulses is selectable over a range of from 0.5 Hz to 10.0 Hz with a fifty percent duty cycle. The master clock pulses are applied to various components in the system as described below. Among these components to which the master clock pulses are applied are two-input AND gate 82 and three-input AND gate 83. The second input signal for AND gate 82 is derived from the sport-/array mode switch 57 in the array mode. The output signal from AND gate 82 is applied to an OR gate 84 to provide count pulses for a binary counter 85. The count registered at counter 85 is reflected in its parallel output lines applied to a demultiplexer which functions to provide N binary output signals, each of which corresponds to a respective count registered in counter 85. The counter may, for example, be embodied by model 74193 standard integrated circuits connected in cascade to provide a count capacity of at least N. Demultiplexer 86 may take the form of standard integrated circuit model number 74154, a sufficient number of these being provided to achieve the requisite number (N) of output lines. N, in this case, corresponds to the number of array lamp positions 17 in the screen 15 at the front panel of housing 10. The N output signal of demultiplexer 86, inverted by inverter 88, provides the second input signal for AND gate 83. The third input signal for that gate is derived from switch 57 in the array mode via a delay unit 87.

The counting mode for counter 85 is determined by the two AND gates 82 and 83. Specifically, when AND gate 82 is enabled in the array mode, the master clock pulses pass continuously through to the counter 85 which continues to count in a spillover mode until the switch 57 is moved to another position or a reset pulse is applied to the counter. In the sport mode counter 85 counts to N and stops. Control for this counting mode is achieved via AND gate 83 which receives the $\overline{N}$ signal from demultiplexer 86 and inverter 88. The $\overline{N}$ signal is high at all times unless the count in counter 85 registers N, at which time AND gate 83 is inhibited from passing the master clock pulses.

The timing logic described above results in the counter spilling over continuously in all modes involving illumination of the lamps at the front panel of housing 10. The only time the counter terminates at a count of N is in the sport mode when the lamps 71 (FIG. 11) on pole 70 are sequentially illuminated. In that mode, a delay provided by delay circuit 87 prevents the count pulses from being passed through AND gate 83 immediately upon switching to the sport mode, thereby providing the subject sufficient time to prepare for the simulated pitch. The reset signal applied to counter 85 via reset switch 61 may also be applied via a delay circuit, similar to circuit 87, in order to provide sufficient time for the subject to prepare before subsequent simulated pitches are activated by the reset switch.

It is also possible to provide a counting mode for counter 85 which permits the counter to terminate its count at a count of N during operating modes involving illumination of the lamps at the front panel of housing 10. A circuit for accomplishing this is illustrated, by way of example, in FIG. 23 to which specific reference is now made. AND gate 90 receives as its three input signals the $\overline{N}$ signal from demultiplexer 86 and inverter 88, the master clock signal from the master clock generator 80, and a delayed version of the random signal provided by switch 58 in the random mode. Specifically, the random signal applied to delay circuit 91 is a positive voltage provided by switch 58. The output signal from AND gate 90 is applied as one of the input signals to OR gate 93. A second input signal to that gate is derived from AND gate 92, the input signals for which are the master clock signal and the sequential signal derived from switch 58. More particularly, the sequential signal is a positive voltage applied to AND gate 92 when switch 58 is in its sequential or pursuit position. The third input signal applied to OR gate 93 is derived from D gate 83 of FIG. 1.

Figure 23:
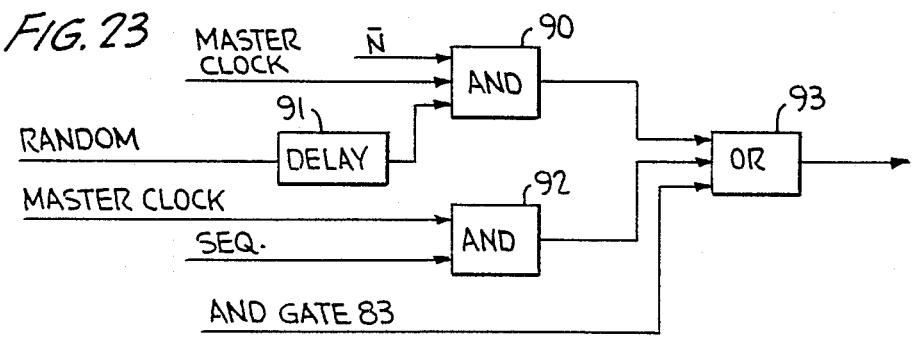
FIG. 23 is a logic diagram of another modification of the master timing circuit of the present invention.

The operation of the circuit in FIG. 23 is such that the output signal from OR gate 93 is applied to counter 85 in FIG. 1. The count pulses are derived from AND gate 90 in the H/E mode at the lamp array and provide a counting mode for counter 85 which causes the counter to terminate after N counts are accumulated. When clock pulses are derived from AND gate 92 a spillover count mode is effected at counter 85. The count mode effected by AND gate 83 is described above and results in a termination of counting when a count N is reached in counter 85.

The output signals from demultiplexer 86 are applied to two sets of N AND gates. In one of these sets of AND gates the individual gates are numbered 101(1)–101(N). In order to conserve space and facilitate an understanding of the invention, only AND gates 101(1), 101(20), 101(34) and 101(N) are actually illustrated. Each of the AND gates 101 receives the sport output signal from switch 57 so that, in the sport mode, the individual gates are activated sequentially as the output lines 1–N are actuated at demultiplexer 86 by the count in counter 85. The output signals from AND gates 101 are applied to the sports mode circuit illustrated in FIG. 18 and described in detail below.

The other set of AND gates receiving the output signals from demultiplexer 86 are designated 102(1)–102(N). In addition to receiving respective output signals from demultiplexer 86, AND gates 102 also receive the array signal from switch 57 so that each successive gate 102 is actuated, in the array mode, by a respective output signal from demultiplexer 86. The output signal from each AND gate 102 is applied to a lamp at each of two lamp positions 17. These lamp positions are designated 17(1)–17(N) in FIG. 15. At each lamp position 17 there are two lamps, namely lamp $L_S$ and lamp $L_R$. The sequential lamp $L_S$ is illuminated during the sequential or pursuit mode as part of a continuous pattern across the array at front panel screen 15. Thus lamp $L_S$ at each lamp position 17 receives the output signal from an AND gate 102 that is actuated at a time during the count sequence of counter 85 which corresponds to the position of that lamp in the continuous pattern of illumination at the front panel. In other words, the output signal from AND gate 102(1) is applied to the lamp $L_S$ at lamp position 17(1); the output signal from AND gate 102(20) is applied to the lamp $L_S$ at lamp position 17(20), etc. The other side of each lamp $L_S$ is connected to the sequential or pursuit terminal of switch 58 which returns the lamp to a reference voltage to complete the circuit. It will be understood, therefore, that as each AND gate 102 is actuated by its corresponding input signal from demultiplexer 86, it illuminates a lamp $L_S$ associated therewith in the pursuit mode.

The output signals from AND gates 102 are also connected to a lamp $L_R$ at each of the lamp positions 17. However, these connections, unlike the connections to lamps $L_S$, are not related to the positional sequence of the lamp positions 17. Thus, for example, the output signal from AND gate 102(1) is connected to the lamp $L_R$ at lamp position 17(20); the output signal from AND gate 102(20) is connected to the lamp $L_R$ at lamp position 17(N); the output signal from AND gate 102(34) is connected to the lamp $L_R$ at lamp position 17(1); the output signal from AND gate 102(N) is connected to the lamp $L_R$ at lamp position 17(34); etc. Lamps $L_R$ are returned to the random (H-E) line of switch 58 so that the lamps may be lit in the random or hand-to-eye mode. It will be seen, therefore, that as counter 85 runs through its count sequence in the random mode, lamp $L_R$ at lamp position 17(20) will be the first lamp to be illuminated; lamp $L_R$ at lamp position 17(N) will be the twentieth lamp to light; lamp $L_R$ at lamp position 17(1) will be the thirty-fourth lamp to be illuminated; and lamp $L_R$ at lamp position 17(34) will be the last lamp to be illuminated.

In the embodiment illustrated in FIG. 15, each switch S at a lamp position 17 receives a signal from the same AND gate 102 that drives the lamp $L_R$ at that lamp position. Thus, in the random mode, each switch S is capable of providing a closure when its associated lamp $L_R$ is energized by an output pulse from an AND gate 102. The output signals provided the closed switch S are designated $S(1) \times L(1)$ through $S(N) \times L(N)$. All of these signals are applied as input signals to a common OR gate 103 which, therefore, receives N input signals. Thus, OR gate 103 will provide an output pulse corresponding to actuation of switch S if that switch S is actuated during illumination of the lamp LR located at the same lamp position 17 as that switch. For example, assume the system is in the random (H-E) mode and at the twentieth count AND gate 102(20) provides an output pulse. This pulse causes the light LR at lamp position 17(N) to be illuminated. If switch S at that lamp position is closed while the output signal from AND gate 102(20) is high, OR gate 103 is actuated by the $S(N) \times L(N)$ signal. Assuming that the fixator lamp is maintained off by switch 59, the output signal from OR gate 103 is applied through one pole of that switch to a counter 104. Counter 104 accumulates all pulses passed by OR gate 103 in the fixator off mode, which pulses are derived by actuation of a switch S while the lamp $L_R$ at the same lamp position 17 is illuminated. The capacity of counter 104 is at least equal to N and its accumulated count is displayed at the count display 51. Thus, during a sequence in which all lamps $L_R$ are illuminated in the random mode, a subject has an opportunity to achieve a count of N at count display 51. If the display registers a number less than N, it is a measure of how many switches S were not timely actuated by the subject during the illumination sequence.

The audio switch 60 also receives the output pulse from OR gate 103 when the fixator lamp is off. When switch 60 is closed it applies these pulses to buzzer 105 to provide a audible indication each time a switch S is timely actuated by the subject.

The output pulses from OR gate 103 are also applied as one input signal to an AND gate 106. The other input signal for AND gate 106 is derived from a fixator clock 107, the output signal from which is designated F. The fixator clock provides a series of output pulses normally at a lower repetition rate than the master clock pulses derived from master clock generator 80. Typically, and as used in the preferred embodiment of the present invention, a ten second period having a sixty percent duty cycle is employed for the fixator clock 107. Each fixator clock pulse causes the fixator lamp 56 at the front panel of housing 10 to be illuminated. In addition, the fixator clock pulses are applied to AND gate 106. The fixator clock 107 is energized only when switch 5 is in its fixator position. Likewise, the output signal from AND gate 106 is permitted to pass to counter 104 only when switch 59 is in the fixator position. AND gate 106 is energized with each successful switch actuation, as designated by an output pulse from OR gate 103, while the fixator clock signal is high. Thus, in the fixator mode, an actuation of switch S while its corresponding lamp LR is illuminated does not cause a count to be registered at counter 104 unless the fixator lamp 56 is also illuminated.

The reset switch 61 is capable of resetting counter 104, counter 85, and other components, as necessary in the system.

Referring specifically to FIG. 16, a circuit is illustrated for illuminating the lamps DS1–DSN in the map array 54 described above in relation to FIG. 10. Each lamp is associated with a respective flip flop 110(1)–110(N). These may be clocked D type flip flops such as integrated circuit types 7474 utilized as data latches. The data input signal for each of flip flops 110 is derived from the output side of a corresponding switch S in the circuit of FIG. 15. Thus, flip flop 110(1) receives its data input signal as signal $S(1) \times L(1)$; flip flop 110(20) receives as its input data signal $S(20) \times L(20)$; flip flop 110(34) receives as input data signal $S(34) \times L(34)$; and flip flop 110(N) receives as its input data signal $S(N) \times L(N)$. The clock input terminal for each of the flip flops 110 is derived from the master clock 80 so that the data appearing on the input data line for each flip flop is changed as each count is registered in counter 85. The Q output signal from each flip flop 110 drives a respective lamp DS1–DSN, which lamps are returned to a reference voltage level. It will be appreciated, therefore, that as each timely switch actuation occurs at a lamp position 17, a corresponding lamp DS1–DS9 is illuminated. Flip flop 110 assures that the illuminated lamp remains illuminated until reset by the reset switch 61 in FIG. 15. Thus, at the end of a cycle illuminating all N lamps $L_R$ in a random mode, an indication is provided, in the form of illuminated lamps DS1–DSN, as to which of the switches S were timely actuated. Those of array lamps DSI–DSN which are not activated in the sequence provide a trainer or optometrist with an indication of potential weaknesses in the tested subject's hand-to-eye coordination. In view of the fact that the map lamps DS1–DSN are arranged in a pattern corresponding to the orientation of lamp positions 17 at the front panel of housing 10, significant groupings of unlit indicators DS1–DSN provides information to the trainer/optometrist as to weaknesses in the field of view of the subject.

It may be desirable, instead of illuminating the lamps in the map array 54 in response to each successful hit by a switch S, that the map lamps are initially illuminated and are extinguished only in response to a successful hit by a switch S. The final indication under such circumstances would result in the lamps DS1–DSN being actuated, at the end of an illumination cycle, only if the switch S at the corresponding lamp position 17 is not timely actuated during the illumination sequence. A circuit for accomplishing this result is illustrated in FIG. 17. The only differences between the circuits of FIG. 17 and 16 are: (1) the $\overline{Q}$ output signal from flip flops 110 are employed to illuminate the lamps DS1–DSN instead of the Q output signal; and a switch is provided in the return line to selectively prevent actuation of the map array lamps DS1–DSN in other than the H-E mode. This latter switch 111 can be eliminated if desired.

The circuitry of FIG. 18, as noted above, relates to the illumination of the lamps 71 utilized in the sports mode and illustrated in FIG. 10. The output signals from AND gates 101(1)–101(N) are individually utilized to energize respective lamps 71(1)–71(N). The signal 101(N-1) utilized to illuminate lamp 71(N-1) is applied to a counter 115 as a start pulse to permit count pulses derived from a sports clock 116 to be successively counted. The repetition rate of the count pulses derived from sports clock 116 is somewhat higher than the repetition rate of the master clock pulses. In fact, it is desirable that the master clock pulses and the sports count pulses be synchronized. This can be achieved, for example, if a common matter oscillator is utilized to drive both clock devices This would permit some number of sports clock count pulses to be counted between the time of occurrence of the 101(N-1) signal and the 101(N) signal which illuminate lamps 71(N-1) and 71(N), respectively. The counting operation at counter 115 is terminated by a stop pulse derived by closure of switch 78 in the bumper 77 (see FIG. 10). As described above, switch 78 closes in response to impact against bumper 77 by a bat, racquet, or other implement or body part swung by the subject. The count registered in counter 115 between the start and stop pulses is a measure of the time at which impact occurs relative to the time that the last lamp 71(N) is illuminated. For example, assume that the repetition rate of the count pulses derived from the sports clock 116 is four times that of the master clock pulses. Under such circumstances, the last lamp 71(N) is illuminated at the time of the fourth sports clock count pulse after the start of the counting procedure by the 101(N-1) signal. If the impact switch 79 is closed while lamp 71(N) is illuminated, the count registered in counter 115 is four. This count is displayed at display unit 117 which may be a digital display corresponding to the number stored in counter 115 or it may be a series of lights wherein each light represents a different count present in counter 115. If the counter stops at count four, the appropriate light or numeral is activated at display 117 indicating to the subject that impact against bumper 77 was properly timed If a count less than four appears after the counter is stopped, an appropriate numeral or lamp is displayed to indicate that the impact was early (i.e., prior to the illumination of the last lamp 71(N). The particular number displayed, or display lamp illuminated, at display 117 is a measure of the degree of how early the impact occurred Similarly, if the count in counter 115 exceeds a count of four upon impact, it is a measure of how late impact was sensed by switch 78 and this is similarly reflected at display 117. Of course, greater resolution in measuring earliness and lateness can be achieved by providing a greater ratio between the repetition rates of the sport clock count pulses and the master clock pulses. It should also be recognized that successive counts 1-N provided by demultiplexer 86 may be spaced in time by more than one master clock pulse. Thus, the output signals from demultiplexer 86 may be arranged to sequence every eighth master clock pulse, for example, so that 8N master clock pulses are required to effect a cycle 1-N at the output lines of demultiplexer 86. Under such circumstances the sports clock count pulses may be derived directly from the master clock pulses as some multiple of the repetition rate of the pulses sequentially appearing on lines 1-N at the output of demultiplexer 86.

Figure 19:
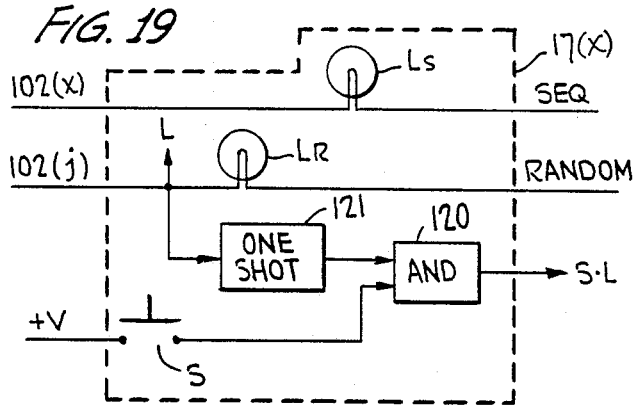
FIGS. 19 and 20 are schematic diagrams of alternative circuits employed at the individual lamp positions in the array at the panel of the apparatus of FIG. 1.

As described above in relation to the circuit of FIG. 15, a timely actuation of switch S is defined as an actuation occurring while the lamp $L_R$ associated with that switch is illuminated. In some embodiments of the invention it may be desirable to provide that a timely actuation of switch S is one which occurs within a predetermined time interval after the onset of illumination of lamp $L_R$, irrespective of whether the lamp $L_R$ is still illuminated at the time switch S is actuated. A circuit for accomplishing this is illustrated in FIG. 19 wherein the lamp position 17(x) is illustrated. In that circuit the closure of switch S provides a high logic level signal at one input terminal of an AND gate 120.

The other input signal applied to that AND gate is derived from a one shot multivibrator 121 triggered at the onset of illumination of lamp $L_R$. The output signal from one shot multivibrator is a high logic level pulse having a duration corresponding to the predetermined period of time within which it is permissible for switch S to be closed, after the onset of illumination of lamp $L_R$, and still constitute a successful hit.

Figure 20:
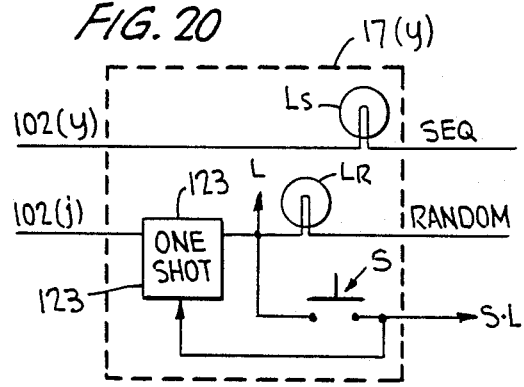

The lamp position circuits 17 described above do not result in lamp $L_R$ being extinguished by a timely actuated switch S. The circuit of FIG. 20 provides for this feature. Specifically, the signal 102(j) derived from the appropriate AND gate 102 in the random mode is applied to a one shot multivibrator 123 instead of being directly applied to the lamp $L_R$ and switch S. The output pulse provided by one shot multivibrator 123 illuminates lamp $L_R$ and passes through switch S if the latter is timely actuated. The resulting pulsed output signal provided through switch S is utilized at OR gate 103 (FIG. 15) in the manner described above. In addition, however, in the circuit of FIG. 20, the timely actuation of switch S resets the one shot multivibrator 123 to terminate the output pulse provided by that device. This serves to extinguish the previously illuminated lamp $L_R$.

Figure 21:
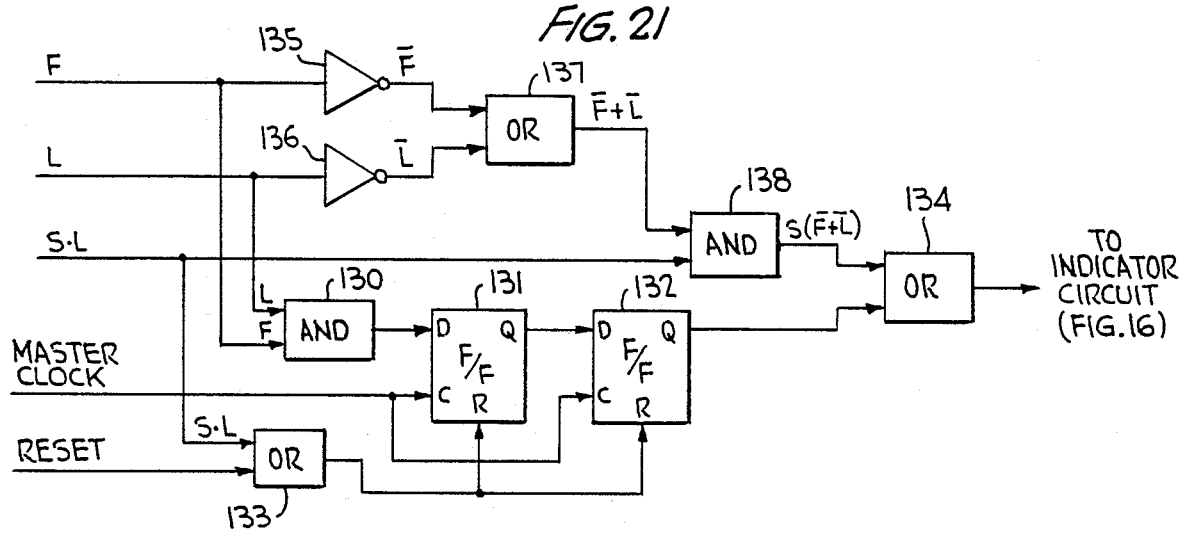
FIG. 21 is a logic diagram of the circuit required to activate the indicators in the map unit of FIG. 10 in the fixator operating mode of the present invention.

The circuit of FIG. 15, combined with the circuits of FIGS. 16 or 17, results in the activating (or deactivating) of the indicators DS1-DSN at the map array 54 in response to each successful hit (i.e., timely actuation by a switch S) at a lamp position 17. In the fixator mode this may not be a desirable characteristic. More particularly, in the fixator mode, the fixator lamp 56 is illuminated at regular intervals for a prescribed period of time. During that prescribed time period plural lamps $L_R$ may be illuminated. It is desirable to have an indication of misses (i.e., absence of timely actuations of switches S when their corresponding lamps $L_R$ are illuminated during a fixator lamp illumination). Simply activating or deactivating an indicator DS1-DSN when its corresponding switch S has been timely actuated does not provide desired information. A circuit for providing this information is illustrated in FIG. 21 to which specific reference is now made. The circuit illustrated in FIG. 1 is one of N such circuits required to actuate a corresponding flip flop 110 in the circuits of FIG. 16 or 17. An AND gate 130 receives the signals L and F as its two input signals. The signal F is the fixator clock signal derived from the fixator clock 107 in the circuit of FIG. 15. The signal L is derived from the signal energizing the lamp $L_R$ in a corresponding lamp position circuit 17 in FIGS. 15, 19 or 20. The output signal from AND gate 130 is applied as the data input signal to a first flip flop 131. The Q output signal from that flip flop is applied as the data input signal to a second flip flop 132. Both of flip flops 131 and 132 are clocked by the master clock signal. The S×L signal from the corresponding lamp position circuit 17 is applied to the reset terminals of both flip flops 131 and 132 via OR gate 133. The reset signal provided by switch 61 is also applied to the reset input terminals of flip flops 131 and 132 via OR gate 133. The Q output signal from flip flop 132 is applied through a further OR gate 134 which applies its output signal to the corresponding data input line of a flip flop 110 in FIGS. 16 or 17.

The Q output signal from flip flop 132 is derived in the following manner. If the $L_R$ lamp at the lamp position circuit 17 in question is illuminated at the same time that the fixator lamp is illuminated, AND gate 130 provides a high level logic signal which sets flip flop 131. If the switch S at the lamp position circuit in question is not actuated before the next master clock pulse, the high level Q output signal from flip flop 131 is clocked into flip flop 132. The resulting high level Q output signal from flip flop 132 is passed through OR gate 134 to the corresponding data input line of a flip flop 110 in the circuit of FIG. 16. In other words, the corresponding DS indicator in the circuit of FIG. 16 is activated if the corresponding panel lamp $L_R$ and the fixator lamp are simultaneously illuminated but the associated switch S is not timely actuated.

The logic described thus far in relation to FIG. 21 may stand alone to provide an indication, in the fixator mode, only when the subject fails to timely actuate a switch S. The additional logic provided for in the circuit of FIG. 21 is optional and may be eliminated, if desired. That additional logic calls for the illumination of an indicator at the map circuit in FIG. 16 if there is an actuation of a switch S at a time where either the fixator lamp or the corresponding $L_R$ is not illuminated. In order to provide this logic the signals F and L are inverted by respective inverters 135 and 136 so that the signals $\overline{F}$ and $\overline{L}$ are applied to an OR gate 137. The output signal from OR gate 137 is applied to AND gate 138. A second input signal for AND gate 138 is derived from the actuated switch S at the lamp position circuit 17. The output signal from AND gate 138 is applied to OR gate 134 so that it may drive the appropriate flip flop 110 in the circuit of FIG. 16.

It is to be borne in mind that the circuit illustrated in FIG. 21 is useful only during the fixator mode. Specifically, it provides meaningful indications at the map array 54 of improper actuations of switches S while the fixator lamp is illuminated. Actuations of the indicators at the lamp array 54 during non-fixator modes may proceed in the manner described in relation to FIGS. 15, 16 and 17. For the latter modes, the output signal from OR gate 134 should be inhibited, as by connecting that output signal to an AND gate enabled only when switch 59 is in the fixator mode. The output from that AND gate would be passed through an OR gate along with the output signal S×L derived from the appropriate lamp position circuit in order to drive corresponding flip flop 110.

Figure 22:
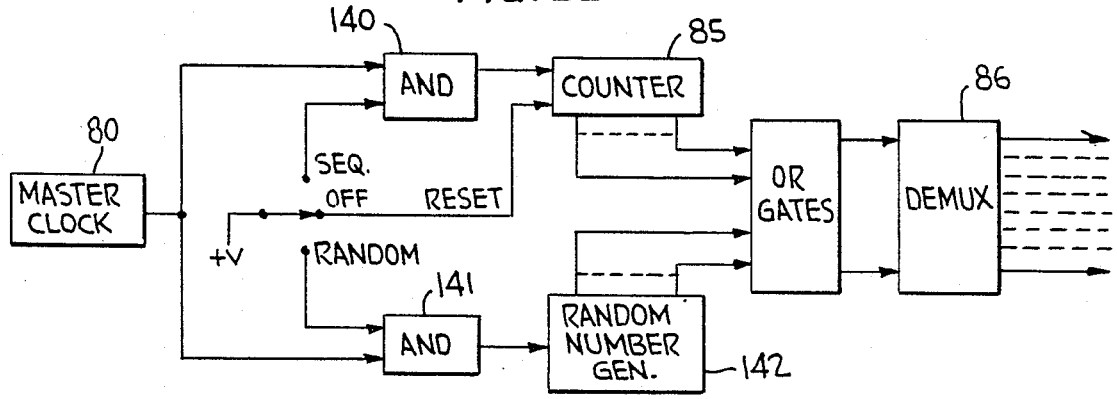
FIG. 22 is a schematic diagram of an alternative master timing circuit capable of providing both sequential and purely random illumination of the lamps at the panel of the apparatus of FIG. 1.

In describing the random mode of operation wherein lamps $L_R$, as opposed to lamps $L_S$, are actuated. The "random" sequence provided by the circuit of FIG. 15 is not random in the true sense; that is, it is random only in that lamps $L_R$ which are successively illuminated are not positioned adjacent on another. This absence of identifiable positional sequencing in the illumination pattern is sufficient, in most cases, to appear to be random to a subject viewing the front panel grid, particularly if there are a large number of lamp positions. However, for some applications it may be desirable to provide a true random sequence. The circuit of FIG. 22 shows a master timing diagram in which this is possible. The master clock 80 provides its master clock pulses to each of two AND gates 140 and 141. AND gate 140 is enabled in the sequential mode while AND gate 141 is enabled in the random mode. The resulting output pulses from AND gate 140 are utilized to increment the count at counter 85 in the manner described above in relation to FIG. 15. The output pulses from AND gate 141 are utilized to clock a random number generator 142. Random number generator 142, each time it is clocked, supplies a unique combination of binary digits at its output terminals. An example of a technique and apparatus for providing these random numbers is described in U.S. Pat. Nos. 3,366,779 (Catherall et al) and 3,798,360 (Feistel). The number of permissable random numbers provided by generator 142 is limited to the N numbers required to actuate AND gates 101 or 102 in FIG. 15. Depending upon the mode of operation, the binary digit output signals from counter 85 or the binary digit output signals from random number generator 142 are applied to the demultiplexer 86 which activates the AND gates 101, 102 in the manner described above.

As described above, the pursuit mode is characterized by the fact that the lamps $L_S$ are actuated in accordance with their positional sequence such that a continuous pattern is formed by the momentarily illuminated lamps. One such pattern for properly exercising the ocular muscles of the subject would be a spiral whereby lamp positions 1-N would be sequentially located along the prescribed spiral path. It is possible, of course, to program a plurality of different patterns to be followed by the sequentially illuminated lamps in the pursuit mode. This, as will be easily recognized by those of ordinary skill in the art, can be effected by appropriate logic interconnected between the output signals from demultiplexer 86 and the various lamp position circuits 17.

The digital display provided on the remote map unit 50 (see FIG. 10) may be duplicated at some location on housing 10 so as to be visible to the subject when standing in front of the lamp panel. For most applications, however, the provision of the audible recognition of successful hit by means of buzzer 105 should suffice to permit the tested subject to be aware of successful hits.

In the particular embodiment illustrated herein, two lamps $L_S$ and $L_R$ are provided at each of the lamp positions 17. This has proven to be convenient to distinguish between the sequential and random operating modes. It will be appreciated, of course, that a single lamp may be provided at each lamp position; under such circumstances, the logic provided to drive that lamp in the sequential mode would be inhibited in the random mode, and vice versa. In addition, although no lamps need be provided at the dummy positions 16 on component board 20, it is contemplated that dummy lamps and switches may be employed, depending upon the transparency of the material employed for screen 15 and actuators 42. The important feature, under any circumstances, is to render each of the dummy positions visually indistinguishable from the actual lamp positions when viewed from in front of the housing 10.

It is to be understood that much of the subject matter illustrated in FIGS. 1-14 is diagrammatic in nature, in some cases lacking obvious details having no bearing on the inventive concepts described herein. For example, although an elongated rod 70 is illustrated in FIG. 10 as the object receiving the impact from a swung bat, tennis racquet, or the like, a significantly more substantial structure may be utilized so as to absorb the impact. The important point is that the last lamp 71 is disposed at the impact point so that the timing of the subject can be accurately monitored. It is also important that the bumper 77 absorb some of the shock of the impact so as to simulate the resistance afforded by an actual ball o other object being simulated.

From the foregoing description it will be appreciated that the present invention makes available a novel vision and hand/eye testing and exercising apparatus and method wherein optical muscles, hand-to-eye coordination and timing of a subject may be accurately and precisely measured as well as exercised.

Having described preferred embodiments of our invention, it is believed that other modifications, variations and changes will be suggested to those skilled in the art in view of the techniques and teachings set forth herein. It is therefore to be understood that all such variations, modifications and changes are believed to fall within the scope of the present invention a defined by the appended claims.

We claim:

1. A vision and hand/eye exercising and testing device comprising:
   a housing having a front panel;
   a multiplicity of lamp positions and dummy positions interspersed on said panel in an array, said lamp positions being substantially visually indistinguishable from said dummy positions when viewed from in front of said panel;
   a first plurality of lamps, each mounted in said housing behind a respective lamp position such that each lamp, when illuminated, is visible from in front of said panel;
   first actuation means for momentarily and sequentially illuminating said first plurality of lamps one at a time in an order determined by said actuation means;
   a plurality of manually actuable switches, one switch for each lamp position, each switch being located on said panel at a respective lamp position so as to be associated with the lamp at that lamp position; and
   logic means for detecting actuation of each switch relative to the time at which the lamp associated with that switch is illuminated.

2. The device according to claim 1 wherein said logic means includes means for sensing and providing a logic signal whenever one of said switches is actuated while its associated lamp is illuminated.

3. The device according to claim 2 further comprising:
   hit counter means for counting said logic signals; and
   display means for displaying the logic signal count accumulated at said hit counter means.

4. The device according to claim 1 wherein said logic means includes means for sensing and providing a logic signal whenever each of said switches is actuated within a predetermined time after onset of illumination of the lamp associated with that switch.

5. The device according to claim 4 wherein said first actuator means includes means for illuminating said lamps sequentially at regular equal time intervals, said device further comprising means for selectively varying said time intervals.

6. The device according to claim 1 further comprising:
   a fixator lamp disposed substantially centrally of said array on said front panel so as to be visible from in front of said panel; and
   means for repeatedly and momentarily illuminating said fixator lamp;
   wherein said logic means includes means for providing a logic signal when the following events occur simultaneously: said fixator lamp is illuminated; a lamp is illuminated at one of said lamp positions; and the switch associated with the illuminated lamp at one of said lamp positions is actuated.

7. The device according to claim 6 further comprising:
   hit counter means for counting said logic signals; and
   display means for displaying the logic signal count at said hit counter means.

8. The device according to claim 6 further comprising:
   a plurality of indicators, each indicator representing a counterpart of a respective lamp in said array; and
   means for activating each indicator when its corresponding array lamp is illuminated while the fixator lamp is illuminated but the switch associated with said corresponding array lamp is not actuated while said corresponding array lamp is illuminated.

9. The device according to claim 1 further comprising control means including:
   a plurality of indicators, each indicator representing a counterpart of a respective lamp in said array; and
   means for activating each indicator in response to its counterpart lamp having been illuminated and the switch associated with that counterpart lamp being actuated within a predetermined time after the onset of illumination of said counterpart lamp.

10. The device according to claim 9 further comprising a substantially transparent marker sheet placeable over said indicators to permit viewing of said indicators and marking of said sheet over each indicator.

11. The vision exercising device according to claim 1 wherein said control means comprises timing adjustment means for selectively varying the time period between successive illuminations of lamps in said order of actuation.

12. A vision and hand/eye exercising and testing device comprising:
    a housing having a front panel;
    a multiplicity of lamp positions and dummy positions interspersed on said panel in an array, said lamp positions being substantially visually indistinguishable from said dummy positions when viewed from in front of said panel;
    a first plurality of lamps, each mounted in said housing behind a respective lamp position such that each lamp, when illuminated, is visible from in front of said panel;
    first actuation means for momentarily and sequentially illuminating said first plurality of lamps one at a time in an order determined by said actuation means;
    a second plurality of lamps disposed in a linear array extending from a proximal position toward an impact location, wherein each successive lamp in said linear array is spaced from a preceding lamp;
    second actuation means for momentarily lighting each lamp in said linear array successively in a sequence from said proximal location toward said impact location;
    protective bumper means for protecting the last lamp in said linear array from damage against impact, said last lamp being located substantially at said impact location;
    switch means responsive to forceful impact against said last lamp for providing a switch closure; and
    comparison means for monitoring the time interval between said switch closure and the illumination of said last lamp.

13. The device according to claim 12 further comprising display means responsive to said comparison means for indicating which occurs first as between said switch closure and the illumination of said last lamp.

14. The device according to claim 12 wherein said bumper means comprises clear plastic means, in which said last lamp and said switch means are embedded, for absorbing impact applied longitudinally of said linear array at said impact location.

15. The device according to claim 12 wherein said first and second actuation means includes a common actuator comprising clock means for providing a continuous series of clock pulses at a determinable repetition rate, master counter means for receiving an counting said clock pulses and registering count values corresponding to the accumulated count of clock pulses, and logic means connected to said master counter means for providing a plurality of actuation pulses on respective actuation pulse lines in response to respective count values registered at said master counter means;

and further comprising:
  manually operable mode selection means for alternatively providing first and second control signals;
  means responsive to said first control signal for enabling application of said actuation pulses to lamps at said first plurality of lamps and inhibiting application of said actuation pulses to said second plurality of lamps; and
  means responsive to said second control signal for enabling application of actuation pulses to lamps in said second plurality of lamps and inhibiting application of s id actuation pulses to said first plurality of lamps.

16. The device according to claim 15 wherein each actuation line provides a respective actuation pulse for a respective lamp in each of said first and second pluralities of lamps.

17. The device according to claim 15 wherein said clock means includes means for manually adjusting said determinable repetition rate.

18. A device for simulating and monitoring a sports activity in which a subject strikes an object moving toward the subject, said device comprising:
  a support;
  a plurality of lamps disposed in a linear array extending from said support toward said subject, wherein each successive lamp in said linear array is spaced from a preceding lamp;
  actuation means for momentarily illuminating each lamp in said linear array successively in a sequence extending from said support toward said subject;
  protective bumper means for protecting the last lamp in said linear array from damage against impact, said last lamp being the lamp closest to said subject;
  switch means responsive to forceful impact against said last lamp for providing a switch closure; and
  comparison means for monitoring the time interval between said switch closure and illumination of said last lamp.

19. The device according to claim 18 wherein said bumper means comprises a plastic member in which said last lamp is embedded to be visible through said plastic and which includes means for absorbing impact applied longitudinally along said array at said impact location.

20. The device according to claim 19 wherein said bumper means includes means for simulating resistance to impact provided by a specific moving object.

21. The device according to claim 18 further comprising display means responsive to said comparison means for indicating which occurs first as between said switch closure and illumination of said last lamp.

22. The device according to claim 21 wherein said display means further comprises means for indicating a measure of the duration of the time interval monitored by said comparison means.

23. The device according to claim 18 further comprising means responsive to said comparison means for providing an indication that said last bumper means has been forcefully impacted while said last lamp is illuminated.

24. The device according to claim 18 further comprising means for adjusting the repetition rate at which said lamps are successively illuminated.

25. The device according to claim 18 further comprising:
  a housing having a front panel and within which said actuation means is located;
  a multiplicity of lamp positions and dummy positions interspersed on said panel in a grid-like array, said lamp position being substantially visually indistinguishable from said dummy positions when viewed from in front of said panel;
  a further plurality of lamps, each mounted in said housing behind a respective lamp position such that each lamp in said further plurality, when illuminated, is visible from in front of said panel; and
  logic means responsive to said actuation means for momentarily and sequentially illuminating said further plurality of lamps one at a time in an order determined by said further actuation means.

26. The device according to claim 25 wherein said display means further comprises means for indicating a measure of the duration of the time interval monitored by said comparison means.

27. The device according to claim 21 further comprising mean responsive to said comparison means for providing an indication that said bumper means has been forcefully impacted while said last lamp is illuminated.

* * * * *